(12) United States Patent
Powell et al.

(10) Patent No.: US 9,222,925 B2
(45) Date of Patent: Dec. 29, 2015

(54) OXYGEN SENSORS AND THEIR USES

(75) Inventors: Jonathan Joseph Powell, Cambridge (GB); Nuno Jorge Rodrigues Faria, Bedford (GB); Carlos Andre Passos Bastos, Cambridge (GB)

(73) Assignee: Medical Research Council, Swindon, Wiltshire (GB)

( * ) Notice: Subject to any disclaimer, the term of this patent is extended or adjusted under 35 U.S.C. 154(b) by 0 days.

(21) Appl. No.: 13/981,433

(22) PCT Filed: Jan. 25, 2012

(86) PCT No.: PCT/GB2012/000076
§ 371 (c)(1),
(2), (4) Date: Sep. 24, 2013

(87) PCT Pub. No.: WO2012/101407
PCT Pub. Date: Aug. 2, 2012

(65) Prior Publication Data
US 2014/0065271 A1    Mar. 6, 2014

(30) Foreign Application Priority Data
Jan. 25, 2011   (GB) .................................. 1101299.4

(51) Int. Cl.
*G01N 31/22* (2006.01)
*G01N 31/00* (2006.01)
*B82Y 30/00* (2011.01)

(52) U.S. Cl.
CPC .............. *G01N 31/225* (2013.01); *B82Y 30/00* (2013.01); *G01N 31/22* (2013.01); *G01N 31/223* (2013.01); *Y10T 436/20* (2015.01); *Y10T 436/207497* (2015.01)

(58) Field of Classification Search
CPC ... G01N 31/225; G01N 31/223; G01N 31/22; G01N 31/00; B82Y 30/00; Y10T 436/20; Y10T 436/207497; Y10T 436/00
USPC .................... 426/232, 231, 87; 436/136, 127; 206/459.1
See application file for complete search history.

(56) References Cited

U.S. PATENT DOCUMENTS

| | | | |
|---|---|---|---|
| 3,663,176 A | 5/1972 | Cagle et al. | |
| 4,169,811 A | 10/1979 | Yoshikawa et al. | |
| 2004/0258562 A1* | 12/2004 | Mills et al. | ...................... 422/57 |
| 2008/0163673 A1 | 7/2008 | Attar et al. | |
| 2008/0300133 A1 | 12/2008 | Langowski et al. | |

FOREIGN PATENT DOCUMENTS

| | | |
|---|---|---|
| DE | 858027 C | 12/1952 |
| GB | 2368908 A | 5/2002 |
| GB | 2462374 A | 2/2010 |
| WO | 2008096130 A1 | 8/2008 |
| WO | 2010/085927 A1 | 8/2010 |

OTHER PUBLICATIONS

Moessmer, R. Machine Translation of WO 2010/085927 Description Section, obtained on Apr. 27, 2015, pp. 1-12.*
Wiberg, Nils, "Lehrbuch der Anorganischen Chemie", vol. 91-100, pp. 1136-1146 (1985).
International Search Report/Written Opinion from corresponding International Application No. PCT/GB2012/000076, issued May 30, 2012.
UK Search Report issued in priority GB Application No. 1101299.4, dated Apr. 20, 2011.

* cited by examiner

*Primary Examiner* — Christine T Mui
(74) *Attorney, Agent, or Firm* — Patrick J. Hagan; Dann, Dorfman, Herrell, and Skillman

(57) ABSTRACT

Oxygen sensors and their uses are disclosed, and more particularly to oxygen sensors for use in product packaging for storing an article in a packaging envelope under modified atmosphere conditions wherein the oxygen sensors comprise solid oxo-hydroxy metal ion materials, optionally modified with one or more ligands and/or optionally having polymeric structures. The sensors may be present in a hydrated, oxygen permeable matrix, for example formed from a material, such as gelatine. The sensors are useful in many technical fields, and find particular application in the field of food packaging as they are safely disposable (e.g. are environmentally friendly), cheap to manufacture, and provide detectable changes in the presence of oxygen that are easy to read.

21 Claims, 4 Drawing Sheets

OXYGEN SENSORS AND THEIR USES

CROSS-REFERENCE TO RELATED APPLICATIONS

This application is the U.S. National Stage of International Application No. PCT/GB2012/000076, filed Jan. 25, 2012, which claims priority from GB 1101299.4, filed Jan. 25, 2011. The entire disclosure of each of the aforesaid applications is incorporated by reference in the present application.

FIELD OF THE INVENTION

The present invention relates to oxygen sensors and their uses, and more particularly to oxygen sensors for use in product packaging for storing an article in a packaging envelope under modified atmosphere conditions.

BACKGROUND OF THE INVENTION

Modified atmosphere packaging, and in particular oxygen-free packaging, are growing in importance for extending the shelf-life of perishable products, such as foodstuffs, or providing a protective atmosphere for other types of sensitive products. However, this growth has been limited by the absence of suitable sensors that can confirm that the oxygen levels are kept at suitably low levels.

This failure in the art is a result of the diverse range of requirements for an ideal sensor. Generally, the sensors need to be inexpensive as packaging cannot incur high costs, especially for consumable products such as foodstuffs. They also need to be safe and non-toxic as they may be in contact with food and leaching may occur, or they may be at risk of accidental ingestion, for example by children. Furthermore the reaction of the sensor to a packaging failure preferably needs to be irreversible under normal packaging environment. This is important as an increase in oxygen level when a packaging failure occurs can lead to spoilage due to growth of microorganisms and it can happen that their metabolic activity restores low oxygen levels. This means that a reversible sensor may show that no packaging failure has occurred. In addition, it would be useful if the sensitivity of the sensor was tailorable as different applications of the packaging may tolerate different oxygen levels. Finally, the sensors should ideally be easy to use, providing an observable change that an unsophisticated user can appreciate, and without recourse to additional equipment, and be easy to incorporate in the packaging.

There are a few products commercially available in the market, namely, Oxy2 Dot® RedEye® and Ageless Eye™. However, they suffer from a range of significant limitations.

The Oxy2 Dot®, which is manufactured by OxySense®, is a fluorescence-based oxygen sensor. The product is a small circle that sticks to the inside of the package and the fluorescence intensity, which is inversely proportional to oxygen level, is measured by a photodetector. The two main problems with this sensor are (a) the need for expensive sensing equipment, and (b) temporary high oxygen levels may go unnoticed as the sensor operates in a reversible manner. The RedEye® operates on similar principles to the Oxy2 Dot® and, therefore, suffers from similar limitations.

The Ageless Eye™, which is manufactured by Mitsubishi Gas Chemical (MGC), changes visible colour upon oxidation. At low oxygen concentrations (<0.1%) the sensor appears pink, but when the oxygen concentration increases the colour changes gradually to blue. The limitations of this sensor are that it is not irreversible, it is expensive (60 p each) and the dye is harmful (methylene blue).

A further product is under development. A UV activated oxygen indicator is currently being developed by Mills. This sensor, which uses the same dye as Ageless Eye™ (methylene blue), is coated onto the inner side of packaging film and is only activated when exposed to UV light, which changes its colour from blue to white. When the sensor is exposed to oxygen, it regains the blue colour. The main issues with this sensor are safety issues due to the use of methylene blue, aesthetic (tainting of food), and the bleaching effect (blue to white) due to prolonged exposure to shelf light, which may lead to false negatives.

There is also a need to develop an effective oxygen sensor for use in non-food related fields, such as packaging pharmaceuticals and nutraceuticals, and for use in other fields, such as the storage of rare books and manuscripts, and for use in the packaging of high value products, such as electronic devices and components.

Oxygen sensing has been developed in other technical fields. U.S. Pat. No. 3,663,176 describes the use of metal salts of elements in Group IVB and VB of the periodic table as a colorimetric oxygen indicator in stream of alkene (olefin) in polymerization processes. US 2008/0300133 discloses an oxygen scavenger and indicator comprising three components: (a) an oxygen sorbent which is a metal or metal compound that can transfer from one oxidation state to another, (b) a redox indicator and/or complexing agent for the metal or the oxidised form of metal, and (c) at least one polymer or gel electrolyte. The oxygen indicator of this application apparently works when the oxidation of the metal causes a change in a physical property of the oxygen sorbent through a change in the interaction with the redox indicator or the complexing agent, such as a colour change.

GB 2,369,808 discloses oxygen or water sensors for food packaging based on a colour change of soluble transition metal compound, generally a soluble coordination complex.

From the discussion above, it will be apparent that the provision of an effective sensor for modified atmosphere packaging, and in particular for packaging for foodstuffs, remains an unsolved problem in the art.

SUMMARY OF THE INVENTION

Broadly, the present invention relates to oxygen sensors and their uses, and more particularly to oxygen sensors for use in product packaging for storing an article in a packaging envelope under modified atmosphere conditions wherein the oxygen sensors comprise solid poly oxo-hydroxy metal ion materials, optionally modified with one or more ligands. In some embodiments, the solid poly-oxo-hydroxy metal ion material is present in a hydrated, oxygen permeable matrix, for example formed from a material, such as gelatine. While the present invention is applicable in many technical fields, it is particularly applicable in the field of food packaging. The presence of oxygen in packaged food leads to food spoilage through enzymatic-catalysed reactions, oxidation of flavours and nutrients and/or by allowing aerobic food-spoiling microorganisms to grow. Modified-atmosphere packaging, in which the food package is flushed with an inert gas such as nitrogen or carbon dioxide, reduces oxygen levels and extends the shelf-live of food products. The market for this packaging is growing but is currently limited by the absence of cheap oxygen monitoring devices, i.e. oxygen sensors, which ensure that low levels of oxygen have been maintained during the storage and handling of the food packages. The present invention addresses this problem through the development of mineral oxo-hydroxide-based sensors that are safely disposable (e.g. are environmentally friendly), cheap to manufacture, and provide detectable changes in the presence of oxygen that are easy to read. Additionally or alternatively, the oxygen sensors of the present invention may be synthesised from food-grade GRAS reagents which makes them inherently safe for food applications.

Thus, the present invention uses solid poly oxo-hydroxy metal ion materials in contrast to the traditional coordination complexes used in US 2008/0300133 that rely on an interaction with a redox indicator to produce detectable changes in response to the presence of oxygen.

Accordingly, in a first aspect, the present invention provides an oxygen sensor comprising a solid poly oxo-hydroxy metal ion material having a transition metal ion in a first oxidation state that is capable of oxidation to a second oxidation state in response to oxygen, wherein the solid poly oxo-hydroxy metal ion material has a polymeric structure in which one or more ligands are non-stoichiometrically substituted for the oxo and/or hydroxy groups, so that exposure of the material to oxygen causes the oxidation of the metal ion in the solid poly-oxo-hydroxy material to produce a detectable change in the material. In some instances in this aspect of the present invention, the solid poly oxo-hydroxy metal ion material is present in a nanoparticulate or nanostructured form.

In a further aspect, the present invention provides an oxygen sensor comprising a solid poly oxo-hydroxy metal ion material having a transition metal ion in a first oxidation state that is capable of oxidation to a second oxidation state in response to oxygen, wherein the solid poly-oxo-hydroxy metal ion material is present in a hydrated, oxygen permeable matrix, so that oxygen permeating the matrix causes the oxidation of the metal ion in the solid poly-oxo-hydroxy material to produce a detectable change in the material.

Alternatively or additionally, the present invention provides an oxygen sensor comprising a solid oxo-hydroxy metal ion material having a transition metal ion in a first oxidation state that is capable of oxidation to a second oxidation state in response to oxygen, wherein the solid oxo-hydroxy metal ion material is present in nanoparticulate or nanostructured form so that exposure of the material to oxygen causes the oxidation of the metal ion in the solid oxo-hydroxy material to produce a detectable change in the material.

Preferably, the metal ion material used in any aspect of the present invention may be dispersed in the matrix in a nanoparticulate or nanostructured form. This helps to increase the surface area of the material that can come into contact with oxygen permeating the matrix. Preferably, in the sensors of the present invention, the metal ion material does not form a soluble complex with materials forming the matrix, as is the case in the system disclosed in US 2008/0300133.

In one embodiment, the oxygen sensor comprises a solid poly oxo-hydroxy metal ion material having a structure in which one or more ligands are non-stoichiometrically substituted for the oxo and/or hydroxy groups. As will be further explained below, this generally means that the ligands are integrated into the solid phase material and have at least some demonstrable metal-ligand bonding.

In a further aspect, the present invention provides a product packaging for storing an article in a packaging envelope under modified atmosphere conditions, wherein the product packaging comprises an oxygen sensor of the present invention within the envelope, so that oxygen leaking into the packaging envelope causes oxidation of the metal ion to produce a detectable change in the material.

In a further aspect, the present invention provides the use of an oxygen sensor as disclosed herein for detecting the leakage of oxygen into product packaging for storing an article in a packaging envelope under modified atmosphere conditions, so that oxygen leaking into the packaging envelope causes oxidation of the metal ion in the oxo-hydroxy material to produce a detectable change in the material.

In a further aspect, the present invention provides a method of detecting oxygen leaking into product packaging for storing an article in a packaging envelope under modified atmosphere conditions, the method comprising:

(a) providing an oxygen sensor of the present invention within the packaging envelope under modified atmosphere conditions, so that oxygen leaking into the packaging envelope causes oxidation of the metal ion in the oxo-hydroxy material to produce a detectable change in the material; and (b) optionally detecting the change in the material to indicate the leakage of oxygen into the packaging envelope.

In a further aspect, the present invention provides a process for producing an oxygen sensor of the present invention, the process comprising:

(a) mixing the solution comprising a transition metal ion, and optionally one or more ligands, in a reaction medium at a first pH(A) at which the components are soluble;

(b) changing the pH(A) to a second pH(B) to cause a solid precipitate or a colloid of the ligand-modified poly oxo-hydroxy metal ion material to be formed;

(c) separating, and optionally drying and/or formulating, the solid poly oxo-hydroxy metal ion material produced in step (b); and (d) optionally processing the solid poly oxo-hydroxy metal ion material so that a nanoparticulate or nanostructured material is produced and/or (e) optionally carrying our one or more post production treatments such as heating.

As explained in more detail below, the process may involve the further step of formulating the solid poly oxo-hydroxy metal ion materials in a matrix by mixing the material, or a precursor thereof, with one or more matrix forming materials to form a hydrated, oxygen permeable matrix capable of sensing oxygen. Alternatively or additionally, the one or more matrix forming materials may be introduced at the time of the reaction to precipitate the solid poly oxo-hydroxy metal ion material so that the process comprises the step of precipitating the solid poly oxo-hydroxy metal ion material in the presence of a solubilized matrix material and solidifying the resulting material to produce a solid poly oxo-hydroxy metal ion material in a semi-solid matrix.

The present invention is based on the recognition that materials containing a redox metal ($M_r$) can convert oxidation state when exposed to a new environment of differing oxygen content or oxidative/reductive potential and that in some cases this will lead to a change in colour in $M_r$-containing materials. The present invention therefore utilises $M_r$-containing materials as sensors of a changing oxygen or oxidative environment. These materials have proven to be highly specific $M_r$-containing materials that are capable of fulfilling one or more of the general requirements of oxygen sensors. These requirements include (1) the need to be inexpensive as usually these are "one off" sensors, (2) environmentally and biologically compatible, especially for uses involving foodstuffs, (3) tailorable to the different sensing needs of different environments and (4) easily read and interpreted as a sensor, preferably without expensive equipment or user training. Generally, for sensors in a solid or semi-solid format, the sensor will include a degree of hydration to facilitate redox activity, while in solution, suspension or gel phase, the sensor is preferably dispersed adequately to provide a large enough surface area that enables sensitive detection. The present inventors have found that some specific manipulation of $M_r$ poly oxo-hydroxides, equally referred to as hydroxy-oxides in the art, fulfils all of the above criteria and provides for sensitive and tailorable sensing of an oxygen environment. Moreover, they have identified that crystalline forms, namely Mr oxides or Mr hydroxides can also be manipulated in such a fashion to allow for useful oxygen sensing. Thus, Mr oxo-hydroxides in their early stages of self-assembly that is polymeric or cross-linked polymeric (denoted "poly") or their more crystalline forms (denoted oxide or hydroxide) can be modified and/or manipulated to usefully sense oxygen levels. it may be clear to those skilled in the art that modification of the materials is likely to lead to a reduction in their crystallinity or an increase in their amorphous nature as described in more detail below.

Embodiments of the present invention will now be described by way of example and not limitation with reference to the accompanying figures and examples.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

The Metal Ion (M)

Figure 1A:
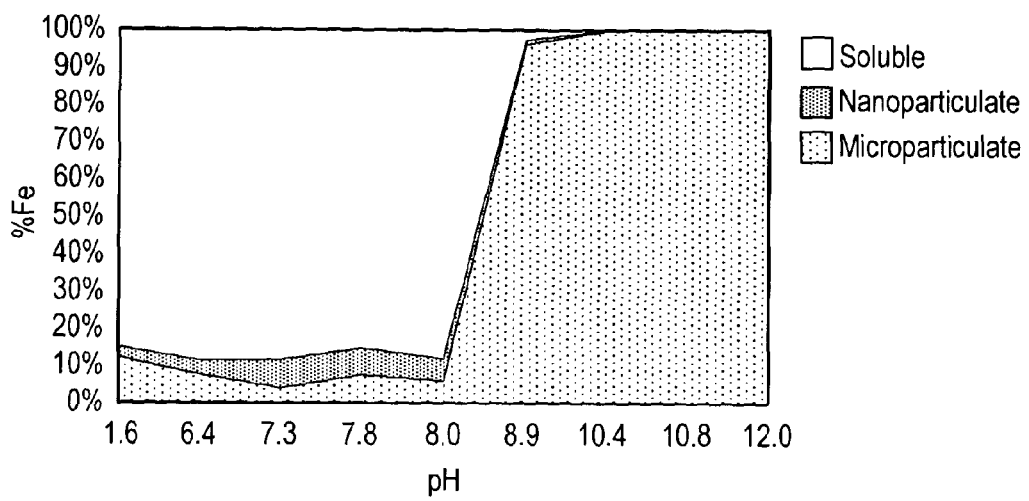
FIG. 1a. Phase distribution during the synthesis of $Fe^{2+}_{40}$OH under nitrogen, where the nomenclature used to describe these materials is described below.

The present invention may employ solid poly oxo-hydroxy metal ion materials as the source of the element of the oxygen sensor that responds to the presence of oxygen. These may or may not be solid ligand-modified poly oxo-hydroxy metal ion materials. The production and characterisation of solid ligand-modified poly oxo-hydroxy metal ion materials is disclosed in our earlier application WO 2008/096130, expressly incorporated by reference in its entirety, and these approaches may also be employed for the production of solid poly oxo-hydroxy metal ion materials, i.e. materials in which ligands are not incorporated into the material. In the materials where ligands are incorporated, the solid ligand-modified poly oxo-hydroxy metal ion materials may be represented by the non-stoichiometric formula $(M_xL_y(OH)_n)$, where M represents one or more metal ions, L represents one or more ligands and OH represents oxo or hydroxy groups, depending on whether the groups are bridging (oxo groups) or surface groups in the solid oxo-hydroxide material. As is well known in the art, non-stoichiometric compounds are chemical compounds with an elemental composition that cannot be represented by a ratio of well-defined natural numbers, i.e. the x, y and n subscripts in the formula above will not necessarily all be natural numbers, even though the materials can be made in a reproducible manner and have consistently reproducible properties.

Conveniently, the solid poly oxo-hydroxides may be formed when the metal ion, originally present in the form of a salt, is dissolved and then induced to form poly oxo-hydroxy materials. This may optionally take place in the presence of one or more ligands (L) and lead to some of the ligand becoming integrated into the solid phase through formal M-L bonding (termed "ligand bonding"), i.e. not all of the ligand (L) is simply trapped in or adsorbed onto the bulk material. The bonding of the metal ion in the materials can be determined using physical analytical techniques such as infrared spectroscopy where the spectra will have peaks characteristic of the bonds between the metal ion and the ligand (L), as well as peaks characteristic of other bonds present in the material such as M-O, O—H and bonds in the ligand species (L). Preferred metal ions (M) are biologically compatible under the conditions for which the materials are used and are readily precipitatable from aqueous solution by forming oxo-hydroxides.

In the present invention, the materials used to form the sensors need to have at least two oxidation states and to produce a detectable change, preferably a visible colour change or a UV-visible change, where the transition metal ion in the materials is oxidised from a first lower oxidation state to a second higher oxidation state, in response to exposure to oxygen or an oxidising environment. It is also preferred that they are biologically compatible materials, especially for applications where they are used in proximity to foodstuffs. These factors mean that the sensors of the present invention are preferably based on transition metal oxo-hydroxides as they typically have the properties required and have the added advantages of being produced by a simple method, easy to incorporate in a semi-solid matrix, safe and undergoing irreversible changes upon exposure to oxygen (under normal packaging conditions). Examples of metal ions include copper, iron, chromium, vanadium, manganese, titanium, cobalt, molybdenum and/or tungsten. Some preferred examples of metal oxidation states that produce the colour changes that may be used in the present invention include: iron ($Fe^{2+}$ to $Fe^{3+}$), copper ($Cu^+$ to $Cu^{2+}$) and cobalt ($Co^{2+}$ to $Co^{3+}$), all of which have the advantage of being non toxic in both oxidation states. It is also preferred that the change in the oxidation state of the metal ion that leads to the colour change is irreversible, or at least is irreversible under the conditions in which it is employed as an oxygen sensor. In some embodiments, more than one type of metal ion (2, 3, 4 or more) may be used.

Without modification, the primary particles of the materials used herein have metal oxide cores and metal hydroxide surfaces and within different disciplines may be referred to as metal oxides or metal hydroxides. The use of the term 'oxo-hydroxy' or 'oxo-hydroxide' is intended to recognise these facts without any reference to proportions of oxo or hydroxy groups. Hydroxy-oxide could equally be used therefore. As described above, the materials of the present invention that are ligand doped are altered at the level of the primary particle of the metal oxo-hydroxide with at least some of the ligand L being introduced into the structure of the primary particle, i.e. leading to doping of the primary particle by the ligand L.

The primary particles of the solid poly oxo-hydroxy metal ion materials described herein are produced by a process referred to as precipitation. The use of the term precipitation often refers to the formation of aggregates of materials that do separate from solution by sedimentation or centrifugation. Here, the term "precipitation" is intended to describe the formation of all solid phase material, including aggregates as described above and solid materials that do not aggregate but remain as non-soluble moieties in suspension, whether or not they be particulate, e.g. nanoparticulate or nanostructured. These forms of the materials have the advantage that the materials can readily be dispersed in a matrix or used in powder form, with high surface areas for reaction with oxygen. The skilled person can readily determine whether materials are nanoparticulate or nanostructured, for example using techniques such as dynamic light scattering, or an equivalent technique, if present as aqueous suspension, or as determined using TEM, or an equivalent technique, if as a powder or in a matrix. Preferably, nanostructured materials include materials whose structural elements—clusters, crystallites or molecules—have dimensions in the 1 to 100 nm range.

In the present invention, reference may be made to the metal oxo-hydroxides having polymeric structures that generally form above the critical precipitation pH. As used herein, this should not be taken as indicating that the structures of the materials are polymeric in the strict sense of having a regular repeating monomer unit because, as has been stated, ligand incorporation (where applicable) is, except by coincidence, non-stoichiometric. The ligand species is introduced into the solid phase structure by substituting for oxo or hydroxy groups leading to a change in solid phase order. The polymeric nature of oxo-hydroxide metal ion materials is discussed in Flynn, Chem. Rev., 84: 31-41, 1984. Alternatively or additionally, for the ligand modified material used in accordance with the present invention, there may be a decrease in the crystallinity of the structure of the material or increase in the disorder that can be determined by high resolution transmission electron microscopy. High resolution transmission electron microscopy allows the crystalline pattern of the material to be visually assessed. It can indicate the primary particle size and structure (such as d-spacing) and give some information on the distribution between amorphous and crystalline material. Using this technique, it is apparent that the chemistry described above increases the amorphous phase of our described materials compared to corresponding materials without the incorporated ligand. This may be especially apparent using high angle annular dark field aberration-corrected scanning transmission electron microscopy due to the high contrast achieved while maintaining the resolution thus allowing the surface as well as the bulk of the primary particles of the material to be visualised.

The reproducible physico-chemical property or characteristic of the materials of the present invention will be dependent on the application for which the material is intended. Examples of the properties that can be usefully modulated using the present invention include: particle size, light absorbing/reflecting properties, hardness-softness, colour, redox capability, dissolution and encapsulation properties. In this context, a property or characteristic may be reproducible if replicate experiments are reproducible within a standard deviation of preferably ±20%, and more preferably ±10%, and even more preferably within a limit of ±5%.

The Ligand (L)

In embodiments of the present invention in which the oxo-hydroxy metal ion materials used to form the oxygen sensors are ligand modified, the solid phase ligand-modified poly oxo-hydroxy metal ion species are represented by the formula $(M_xL_y(OH)_n)$, where L represents one or more ligands or anions that can be incorporated into the solid phase ligand-modified poly oxo-hydroxy metal ion material. By way of example, the ligands may be used to modulate one or more of the following properties: the colour of the material before and after exposure to oxygen, the rate of (colour) change in response to oxygen, the sensitivity of the response to oxygen, i.e. the level of oxygen, for example less than 0.1%, or less than 0.5%, or less than 1.0% or less than 5.0%, needed to induce the detectable change or the kinetics of the response to oxygen or an oxidising environment.

In the materials described herein, preferred examples of the ligands may include one or more of the following types of ligand.

(a) a classical anion ligand selected from phosphate, sulphate, silicate, selenate and/or bicarbonate; and/or (b) a food additive ligand, such as maltol and ethyl maltol; and/or (c) an amino acid ligand, such as tryptophan, glutamine or histidine; and/or (d) a nutrient-based ligand, such as folate, ascorbate or niacin; and/or (e) a carboxylic acid ligand, such as gluconic acid or lactic acid; and/or (f) pendant groups from a semi-solid matrix, e.g. amino acid side chains of gelatin.

Carboxylic acid ligands may be employed, such as linear dicarboxylic acid ligands. Examples of these include ligands represented by the formula HOOC—$R_1$—COOH, where $R_1$ is an optionally substituted alkyl, alkenyl or alkynyl group, or an ionised form thereof, e.g. $R_1$ is a $C_{1-10}$ alkyl group, wherein $R_1$ is optionally substituted with one or more hydroxyl groups. Specific examples of these ligands include succinic acid, malic acid, adipic acid, glutaric acid, pimelic acid, citric acid, aspartic acid or tartaric acid, or an ionised forms thereof, i.e. where the ligand is succinate, malate, adipate, glutarate, pimelate, citrate, aspartate or tartrate.

Whether the carboxylic acid ligand is present as the acid or is partially or completely ionised and present in the form of a carboxylate anion will depend on a range of factors such as the pH at which the material is produced and/or recovered, the use of post-production treatment or formulation steps and how the ligand becomes incorporated into the poly oxo-hydroxy metal ion material. In some embodiments, at least a proportion of the ligand will be present in the carboxylate form as the materials are typically recovered at pH>4 and because the interaction between the ligand and the positively charged metal ion would be greatly enhanced by the presence of the negatively charged carboxylate ion. For the avoidance of doubt, the use of carboxylic acid ligands in accordance with the present invention covers all of these possibilities, i.e. the ligand present as a carboxylic acid, in a non-ionised form, in a partially ionised form (e.g., if the ligand is a dicarboxylic acid) or completely ionised as a carboxylate ion, and mixtures thereof.

Without wishing to be bound by any particular theory, the present inventors believe that the ligand may be provided as pendant groups from matrix material in which the metal oxo-hydroxide is immobilised and/or dispersed. For example, a semi-solid matrix such as gelatine may be used to immobilise and disperse the sensors such that some of side chains of the amino acids in gelatin may be incorporated in surface of primary particle of the poly oxo-hydroxy metal ion material, thus altering its physicochemical properties.

Typically, ligands are incorporated in the solid phase poly oxo-hydroxy metal ion materials to aid in the modification of a physico-chemical property of the solid material, e.g. as compared to a poly oxo-hydroxylated metal ion species in which the ligand(s) are absent. In some embodiments of the present invention, the ligand(s) L may also have some buffering capacity. Examples of ligands that may be employed in the present invention include, but are by no means limited to: carboxylic acids such as adipic acid, glutaric acid, tartaric acid, malic acid, succinic acid, aspartic acid, pimelic acid, citric acid, gluconic acid, lactic acid or benzoic acid; food additives such as maltol, ethyl maltol or vanillin; 'classical anions' with ligand properties such as bicarbonate, sulphate, nitrite, nitrate and phosphate; mineral ligands such as silicate, borate, molybdate and selenate; amino acids such as tryptophan, glutamine, proline, valine, or histidine; and nutrient-based ligands such as folate, ascorbate, pyridoxine or niacin or nicotinamide. Typically ligands may be well recognised in the art as having high affinity for a certain metal ion in solution or as having only low affinity or not be typically recognised as a ligand for a given metal ion at all. However, we have found that in poly oxo-hydroxy metal ion materials, ligands may have a role in spite of an apparent lack of activity in solution. Typically, one ligand or two ligands of differing affinities for the metal ion are used in the production of these materials although zero, one, two, three, four or more ligands may be useful in certain applications.

For many applications, ligands need to be biologically compatible under the conditions used and generally have one or more atoms with a lone pair of electrons at the point of reaction. The ligands include anions, weak ligands and strong ligands. Ligands may have some intrinsic buffering capacity during the reaction.

The ratio of the metal ion(s) to the ligand(s) (L) is also a parameter of the solid phase ligand-modified poly oxo-hydroxy metal ion materials that can be varied according to the methods disclosed herein to vary the properties of the materials. Generally, the useful ratios of M:L will be between 10:1, 5:1, 4:1, 3:1, 2:1 and 1:1 and 1:2, 1:3, 1:4, 1:5 or 1:10.

Throughout the examples, the $M^{i+}_j OH-L_k$ nomenclature was adopted to describe the preparation for ligand-modified poly oxo-hydroxy transition metal materials; where 1) M refers to the transition metal, i+ to its valence, and j its concentration in the initial solution prior to synthesis and 2) L refers to a ligand and k to its concentration. There is no limit to the number of ligands and where no ligand was present the nomenclature used was $M^{i+}_j OH$. for example, the nanoparticulate poly oxo-hydroxy material defined as $Fe^{2+}_{40}OH$-$Tart_{200}$ was prepared from an initial solution that contained 40 mM ferrous iron and 200 mM tartaric acid. Additional to the modified or unmodified poly-oxo-hydroxy materials produced for oxygen sensing, it was shown that more crystalline analogues, namely hydroxides and oxides may also be employed. These more crystalline structures may be initially similarly prepared through aqueous precipitation in the presence of ligand but reacting conditions are chosen to ensure crystallinity is achieved, which typically is assessed through X-ray diffraction measurements. It will however be clear to those in the art that additional methods exist for the conversion of poly oxo-hydroxy phases to crystalline phases including the use of heat.

Producing and Processing the Materials Used to Make Oxygen Sensors

Generally, the materials of the present invention may be produced by a process comprising:
 (a) mixing the solution comprising transition metal ion and optionally one or more ligands in a reaction medium at a first pH(A) at which the components are soluble;
 (b) changing the pH(A) to a second pH(B) to cause a solid precipitate or a colloid of the optionally ligand-modified poly oxo-hydroxy metal ion material to be formed;
 (c) separating, and optionally drying and/or formulating, the solid poly oxo-hydroxy metal ion material produced in step (b); and
 (d) optionally processing the solid poly oxo-hydroxy metal ion material so that a nanoparticulate or nanostructured material is produced; and/or
 (e) optionally carrying our one or more post production treatments such as heating.

In cases where the ligands are provided by the materials forming a semi-solid matrix, the process may involve the step of precipitating the solid poly oxo-hydroxy metal ion material in the presence of one or more solubilized matrix materials and solidifying the resulting material to produce a solid poly oxo-hydroxy metal ion material in a semi-solid matrix. While not wishing to be bound by any particular theory, the present inventors believe that in such materials the pendant groups from the semi-solid matrix are capable of acting as ligands in the solid poly oxo-hydroxy metal ion materials.

It will be apparent that as the materials used to form the oxygen sensors are oxidisable in the presence of atmospheric oxygen, it is advisable to prepare them under an inert atmosphere or reduced oxygen conditions. Examples of other conditions that may be employed include the following using a first pH(A) which is less than 2.0 and the second pH(B) which is between 3.0 and 12.0, preferably between 3.5 and 8.0, and more preferably between 4.0 and 6.0, and carrying out the reaction at room temperature (20-25° C.). In general, it is preferred that in step (a), the solution contains 20 to 100 mM $Fe^{3+}$ and 0 to 250 mM of a suitable carboxylic acid ligand, and more preferably about 40 mM $Fe^{3+}$ and <100 mM of the ligand. If a ligand is used then a preferred ligand is tartaric acid.

The separation of a candidate material may then be followed by one or more steps in which the material is characterised or tested. Examples of further steps or post production treatments include, but are not limited to: heating, washing, centrifugation, filtration, spray-drying, freeze-drying, vacuum-drying, oven-drying, dialysis, milling, granulating, encapsulating, embedding (e.g. in gelatine), tableting, mixing, compressing, nanosizing and micronizing.

When these materials are used as oxygen sensors, the further steps include forming the solid poly oxo-hydroxy metal ion material into the format in which it is to be employed as an oxygen sensor. By way of example, the solid poly oxo-hydroxy metal ion material may be dispersed in matrix forming materials such as gelatine to form a semi-solid matrix, mixed with water to form an aqueous suspension, or coated or spray dried on a substrate to provide a sensor in the form of a powder coating.

It should be noted that different sizes and shapes of sensors may be used to control sensing time. For example, sensing materials produced in shallower moulds, than those described herein, will change colour faster, since oxygen will permeate shorter distances through the semisolid matrix before reaching the entirety of the sensing material.

Hydroxy and Oxo Groups

The present invention may employ any way of forming hydroxide ions at concentrations that can provide for hydroxy surface groups and oxo bridging in the formation of these poly oxo-hydroxy materials. Examples include but are not limited to, alkali solutions such as sodium hydroxide, potassium hydroxide and sodium bicarbonate, that would be added to increase [OH] in an ML mixture or $M^{(+)}$ solution, or acid solutions such as mineral acids or organic acids, that would be added to decrease [OH] in an ML mixture or $M^{(+)}$ solution.

The conditions used to produce the compositions of the present invention may be tailored to control the physicochemical nature of the precipitate, or otherwise assist in its collection, recovery or formulation with one or more excipients. This may involve purposeful inhibition of agglomeration, or the use of drying or grinding steps to subsequently affect the material properties. However, these are general variables to any such system for solid extraction from a solution phase. After separation of the precipitated material, it may optionally be dried before use or further formulation. The dried product may, however, retain some water and be in the form of a hydrated solid phase ligand-modified poly oxo-hydroxy metal ion material. It will be apparent to those skilled in the art that at any of the stages described herein for recovery of the solid phase, excipients may be added that mix with the solid poly oxo-hydroxy metal ion material, but do not modify the primary particle and are used with a view to optimising formulation for the intended function of the material. Examples of these could be, but are not limited to, glycolipids, phospholipids (e.g. phosphatidyl choline), sugars and polysaccharides, sugar alcohols (e.g. glycerol), polymers (e.g. polyethyleneglycol (PEG)) and taurocholic acid.

Uses

The oxygen sensors of the present invention may be employed in a range of applications, in particular in the area of packaging and storage, especially where the storage is under modified atmosphere conditions that generally use nitrogen and/or carbon dioxide in a packaging envelope. Accordingly, the sensors may be used for packaging and/or storing products as diverse as food products, pharmaceutical products, nutraceutical products, documents, books or manuscripts, or electronic devices or components.

Materials and Methods

All chemicals were purchased from Sigma Aldrich (Dorset, UK), except uncoloured beef gelatine, which was from a commercial supplier (Oetker).

Synthesis of Metal Oxo-Hydroxides for Use as Oxygen Sensors

The metal oxo-hydroxides described herein are produced by raising the pH of an initial solution containing, at least, a soluble transition metal in a low oxidation state that can undergo oxidation to a higher oxidation state, such as $Fe^{2+}$ or $Cu^+$. This initial solution is typically acidic, at 1.0>pH>7.0, but higher pHs can also be used, providing that the metal can remain soluble under such initial conditions. This initial solution can optionally contain one or one or more ligands of the types described herein such as tartaric acid or succinic acid. Furthermore, an electrolyte, such as NaCl or KCl, can also be added to the initial solution. Subsequently, an oxo-hydroxide material is formed through a process of colloid formation and/or precipitation by gradually increasing the pH (e.g. NaOH) until a suitable pH is achieved. Precipitation is typically carried out at room temperature (20-25° C.), but higher temperatures can also be used, if required. Depending on the intended application, reducing compounds, including reducing sugars such as glucose or fructose can be added at any point during the synthesis process for the purpose of tailoring the sensitivity of the materials to oxygen. Finally, the mineral formed can be recovered through a range of strategies dependent on the nature of the mineral and the intended application. Note that the synthetic process should be carried out, preferably, under low oxygen conditions since this prevents the oxidation of the initial soluble metal or the subsequently produced metal oxo-hydroxide. Low oxygen conditions can be achieved through a range of strategies, such as nitrogen flow, that are not described herein. The synthesis of more crystalline sensors, alternatively the conversion of previously produced amorphous materials described elsewhere in the examples to more crystalline phases can be achieved using similar conditions to those described above. However, higher pH's (pH>11) and/or higher temperatures (>60° C.) may be employed in their synthesis.

Post-Synthesis Recovery and Testing

The techniques used for the post-synthesis recovery of metal oxo-hydroxides of the present invention was dependent on the application and nature of the minerals synthesised. The metal oxo-hydroxides can be recovered by a range of methods such as filtration or centrifugation. In examples below, the metal oxo-hydroxides were tested as (i) aqueous suspensions, (ii) dry powders, or (iii) as part of a semi-solid matrix.

Aqueous Suspensions

Upon synthesis, nanoparticulate metal oxo-hydroxides remain stable in suspension and can be used directly for oxygen sensing. Upon exposure to atmospheric oxygen, or any other source of oxygen, the nanoparticulate material undergoes a process of oxidation with an associated change in colour or UV absorbance change that can be monitored.

Dry Powders

Upon synthesis, metal oxo-hydroxides can be dried and used for oxygen sensing as dry powders. The metal oxo-hydroxide powder can be dried directly from a final suspension or from a pellet obtained by centrifugation, filtration, or ultrafiltration. Upon exposure to atmospheric oxygen, or any other source of oxygen, the dry material undergoes a process of oxidation with an associated change in colour that can be used for oxygen sensing. The powders may also be incorporated in paint or spray coating compositions for ease of application.

Semi-Solid Matrix

Upon synthesis, the metal oxo-hydroxides can be incorporated into a semi-solid matrix, such as a gelatine matrix, that immobilises and disperses the material in a nanoparticulate form. It may also disperse materials which, in the absence of semi-solid matrix, would have remained as micron-sized agglomerates. By way of example, the matrix can be produced by dissolving a gelatine powder such as beef gelatine in an aqueous suspension of metal oxo-hydroxides and subsequently cooling it down, resulting in the formation of a semi-solid matrix. Alternatively, the matrix may be produced as part of the reaction that is used to form the metal oxo-hydroxide. Conveniently, the gelatine is used in an amount between 10-20% w/w. Upon exposure to atmospheric oxygen, or any other source of oxygen, the metal oxo-hydroxide, which is within the semi-solid matrix undergoes a process of oxidation with an associated change in colour that can be used for oxygen sensing.

Examples of materials that may be used as semi-solid matrices for retaining the oxygen sensing materials of the present invention in a disperse and, preferably, nanoparticulated form include hydrocolloids or hydrogels from biological sources such as, but not limited to:

Gelatine (e.g. beef, pork), Pectins, Starches (e.g. maize, wheat, tapioca, potato, etc), starch derivatives (e.g., Carboxy Methyl Starch, Starch Phosphate), cellulose, cellulose derivatives (e.g. Hydroxyethyl Cellulose, carboxymethylcellulose), Plant Gums (e.g. Arabic, Guar Karaya, Locust bean, Tragacanth, Psyllium seed, Quince seed, xanthan, larch, gatti), algae-derived gums (Alginate, Carrageen, agar, agarose, Furcellaran), bacteria-derived sugars (e.g. dextran), or chitosans.

Hydrocolloids or hydrogels from synthetic organic polymers such as, but not limited to, poly(vinyl alcohol) [PVA], poly(acrylic acid) [PAA], poly(ethylene glycol) [PEG] poly (acrylonitrile) [PAN].

Hydrocolloids or hydrogels from inorganic polymers such as, but not limited to, silicate, silicon dioxide, magnesium aluminium silicate, other silicon based gels, aluminium hydroxide, bentonite, other aluminium based gels, or borate based gels.

One consequence of the inclusion of the materials in matrices is that the present inventors have found that some variation in the colour of the sensor may be engineered through the choice of matrix material and the conditions (such as pH) used to make the oxygen sensor. This provides a further means in addition to the use of ligand modification discussed above to tailor different oxygen sensors for particular applications. By way of example, if gelatine were added to a suspension of $Fe^{2+}_{40}OH$ the semi-solid matrix containing ferrous nanoparticles would appear intense bright green whereas the suspension would appear darker (blacker) green. Interestingly, once oxidised the gelatine-based matrix would become bright red whereas the gelatine-free suspension would become brown/orange.

Phase Distribution During Synthesis

A similar procedure to that described above in "Synthesis of metal oxo-hydroxides for use as oxygen sensors" was carried out except that several aliquots were collected at different pH's during synthesis. First, an initial aliquot was also collected for analysis of the "starting metal" concentration. Next the pH was slowly increased by drop-wise addition of a concentrated solution of NaOH with constant agitation until the mixture reached a basic pH (generally >8.0). At different points during the titration, a homogeneous aliquot (1 mL) of the mixture was collected and transferred to an Eppendorf tube. Any centrifugable phase formed was separated from the solution by centrifugation (10 minutes at 13000 rpm). The iron concentration in the supernatant fraction was then determined by ICPOES. To differentiate between soluble iron and particulated non-centrifugable iron (generally <15 nm diameter nanoparticles) in the supernatant, at each time point, each aliquot was also ultrafiltered (Vivaspin 3,000 Da molecular weight cut-off polyethersulfone membrane, Cat. VS0192, Sartorius Stedium Biotech GmbH, Goettingen, Germany) and again analysed by ICPOES.

Inductively Coupled Plasma Optical Emission Spectrometry Analysis (ICPOES)

Metal contents of solutions were measured using a JY2000-2 ICPOES (Horiba Jobin Yvon Ltd., Stanmore, U.K.). Solutions were diluted in 1-7.5% nitric acid prior to analysis.

TEM Analysis

The normal fixation pellet was then dehydrated through the alcohol/acetylnitrile gradient before being fixed in non-aqueous Quettol resin for 7 days. The non-aqueous pellet was resuspended straight into 100% ethanol, overnight, followed by resuspension in acetylnitrile and finally resin. The resultant resin embedded pellets were sectioned in 100 nm thick sections on 400 mesh copper grids for TEM analysis.

Oxygen Analysis

Oxygen levels were monitored using an oxygen meter (Rapidox 1100, Cambridge Sensotec, Cambridge, UK).

Particle Size Analysis

The hydrodynamic particle size of nanoparticulate suspensions was determined by dynamic light scattering (DLS), using a Zetasizer Nano-ZS (Malvern Instruments, UK). The hydrodynamic particle size of the larger agglomerates was determined by static light diffraction (SLD), using a Mastersizer 2000 (Malvern Instruments, UK).

EXAMPLES

Example 1

Ferrous Oxo-Hydroxide, $Fe^{2+}_{40}OH$

All solutions/suspensions were bubbled with nitrogen before and throughout the synthesis to achieve low oxygen conditions. A ferrous solution was prepared by adding ferrous sulphate to water that had been previously acidified with hydrochloric acid. The final iron concentration was 40 mM and the pH was generally below 4.0 and usually about 2.0. Once all of the ferrous salt dissolved, the pH was raised with a 5M NaOH solution to pH 7.0-9.0, usually 8.0, during which a green precipitate consisting of micron sized agglomerates, i.e. ferrous oxo-hydroxide, was formed. Finally, this material was incorporated as a nanoparticulate dispersion in a semi-solid matrix.

Example 2

Nanoparticulate Tartrate Modified Ferrous Oxo-Hydroxide, $Fe^{2+}_{40}OH-T_{200}$ All solutions/suspensions were bubbled with nitrogen before and throughout the synthesis to achieve low oxygen conditions. A ferrous solution was prepared by adding ferrous sulphate to water that had been previously acidified with hydrochloric acid and agitated until all of the ferrous salt dissolved. This solution was then added to another solution containing tartaric acid. The solution obtained from mixing the two solutions contained 40 mM iron and 200 mM tartaric acid, and its pH was generally below 4.0 and usually about 2.0. The pH was then raised with a 5 M NaOH solution to pH 7.0-9.0, usually 8.0, during which a green nanoparticulate suspension, i.e. ferrous oxo-hydroxide nanoparticles, was formed. Finally, this suspension was used directly as a sensor, recovered through filtration for other oxygen sensing methods, or, preferably, incorporated as a nanoparticulate dispersion in a semi-solid matrix.

Example 3

Nanoparticulate Tartrate Modified Ferrous Oxo-Hydroxide, $Fe^{2+}_{40}OH-T_{120}$ Example 2 was repeated using 120 mM tartaric acid as the ligand instead.

Example 4

Nanoparticulate Tartrate- and Succinate-Modified Ferrous Oxo-Hydroxide, $Fe^{2+}_{40}OH-T_{200}Succ_{200}$ Example 2 was repeated using 200 mM succinic acid in addition to 200 mM tartaric acid.

Example 5

Succinate-Modified Ferrous Oxo-Hydroxide, $Fe^{2+}_{40}OH\text{-}Succ_{200}$

All solutions/suspensions were bubbled with nitrogen before and throughout the synthesis to achieve low oxygen conditions. A ferrous solution was prepared by adding ferrous sulphate to water that had been previously acidified with hydrochloric acid and agitated until all of the ferrous salt dissolved. This solution was then added to another solution containing succinic acid. The solution obtained from mixing the two solutions contained 40 mM iron and 200 mM succinic acid, and its pH was about 2.0. The pH was then raised with a NaOH solution to pH 6.5-9.0, usually 8.0, during which a green precipitate, i.e. succinate modified ferrous oxo-hydroxide, was formed. Finally, this suspension was used directly as a sensor, recovered through filtration for other oxygen sensing methods, or, preferably, incorporated as a nanoparticulate dispersion in a semi-solid matrix.

Example 6

Ferrous Oxo-hydroxide, $Fe^{2+}_{40}OH$ Produced with Disodium Carbonate

A ferrous oxo-hydroxide material was prepared as in Example 1 and except 2.5M $Na_2CO_3$ was used instead of 5M NaOH. Finally, this material was incorporated as a nanoparticulate dispersion in a semi-solid matrix.

Example 7

Dry Nanoparticulate Tartrate Modified Ferrous Oxo-hydroxide, $Fe^{2+}_{40}OH\text{-}T_{200}$ A nanoparticulate suspension was prepared as in Example 2. This suspension was then evaporated in a rotavapor at 60° C. under vacuum. Once dry the powder was ground and could be used for sensing oxygen.

Example 8

Ferrous Oxo-Hydroxide Dispersed in a Gelatin Semi-Solid Matrix

The following process was carried out under a nitrogen atmosphere. A ferrous oxo-hydroxide material was prepared as described in Example 1 or 5. Next, beef gelatine (15% w/w) was added to this suspension while stirring. Then, the mixture was heated to 40° C. to dissolve the gelatine. Once the gelatine was fully dissolved, the pH was re-adjusted back to its original level with a NaOH solution. Finally, a semi-solid matrix that immobilised and dispersed the ferrous oxo-hydroxide into nanoparticles was formed by cooling this suspension to room temperature. Note that different sizes and shapes of sensors could be achieved by transferring aliquots of the final suspension to suitably shaped and sized moulds prior to cooling.

Example 9

Nanoparticulate Ferrous Oxo-Hydroxide Immobilised in a Gelatin Semi-Solid Matrix The following process was carried out under a nitrogen atmosphere. A nanoparticulate ferrous oxo-hydroxide was prepared as described in the Examples 2, 3 or 4. Next, beef gelatine (15% w/w) was added to this suspension while stirring. Then, the mixture was heated to 40° C. to dissolve the gelatine. Once the gelatine was fully dissolved, the pH was re-adjusted back to its original level with a NaOH solution. Finally, a semi-solid matrix that immobilised the ferrous oxo-hydroxide nanoparticles was formed by cooling this suspension to room temperature.

Figure 1B:
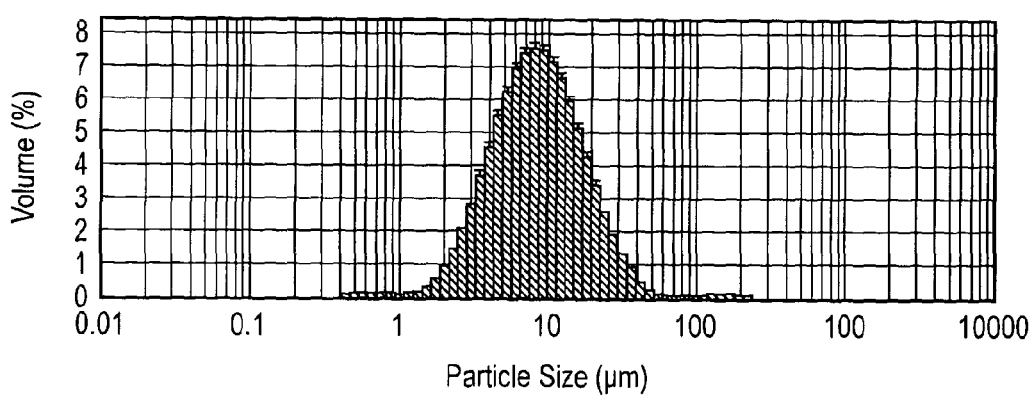
FIG. 1b. Particle size of $Fe^{2+}_{40}$OH prior to incorporation into a gelatine showing that, without modification, it would form large agglomerates (N=3).
Figure 1C:
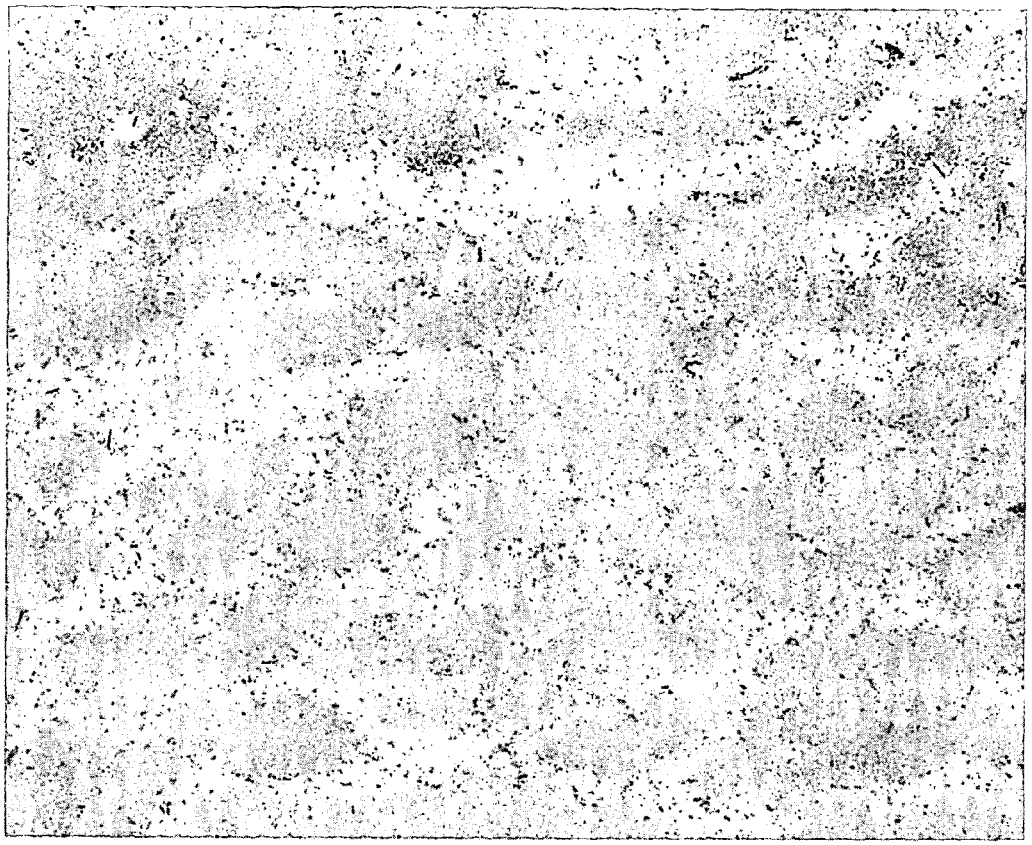
FIG. 1c. TEM image of 2-15 nm $Fe^{2+}_{40}$OH nanoparticles dispersed in a gelatine matrix. The nanoparticles (shown as small dark rods in the TEM image) were produced and incorporated in a gelatine matrix as described in Example 8 and then allowed to oxidise by exposure to air.
Figure 2A:
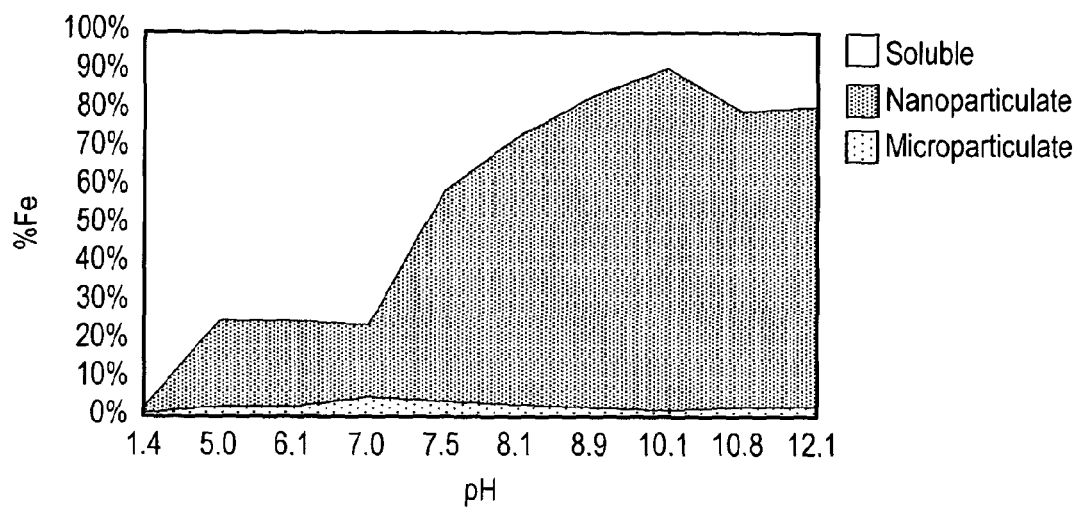
FIG. 2a. Phase distribution during the synthesis of $Fe^{2+}_{40}$OH-$T_{200}$.
Figure 2B:
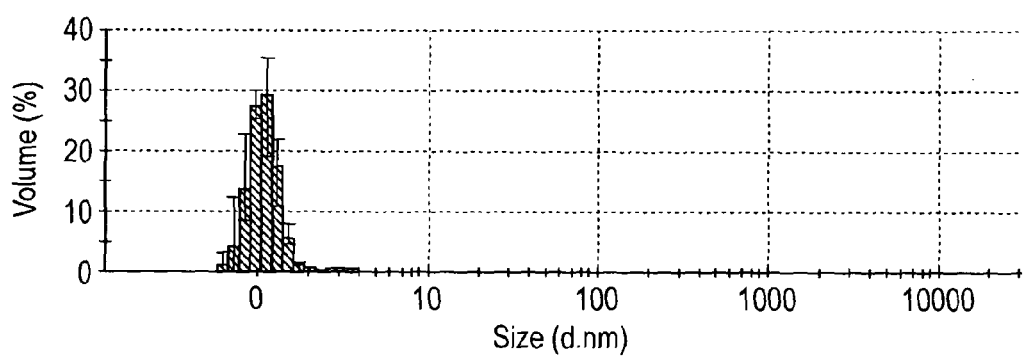
FIG. 2b. Particle sizing for $Fe^{2+}_{40}$OH-$T_{200}$ nanoparticles after synthesis (N=3).
Figure 3:
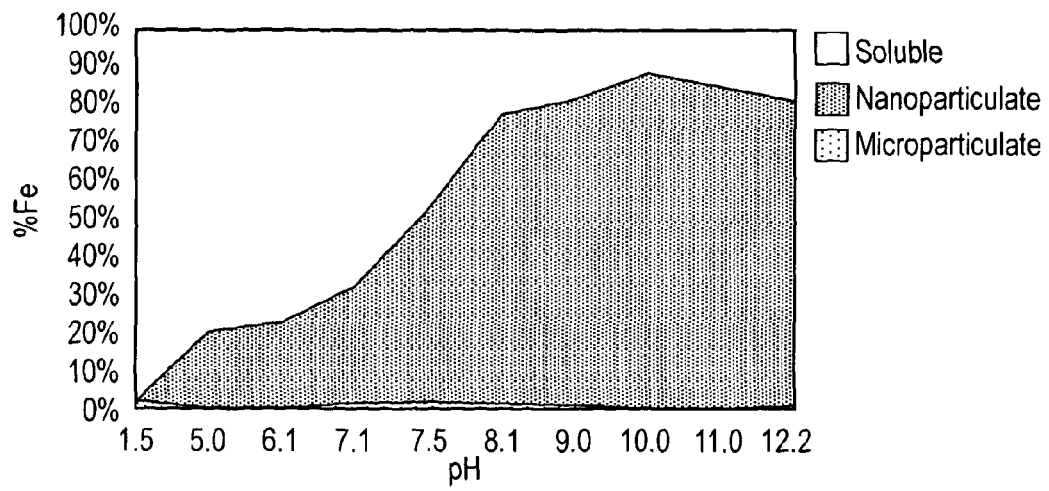
FIG. 3. Phase distribution during the synthesis of $Fe^{2+}_{40}$OH-$T_{200}$Succ$_{200}$ under nitrogen.
Figure 4:
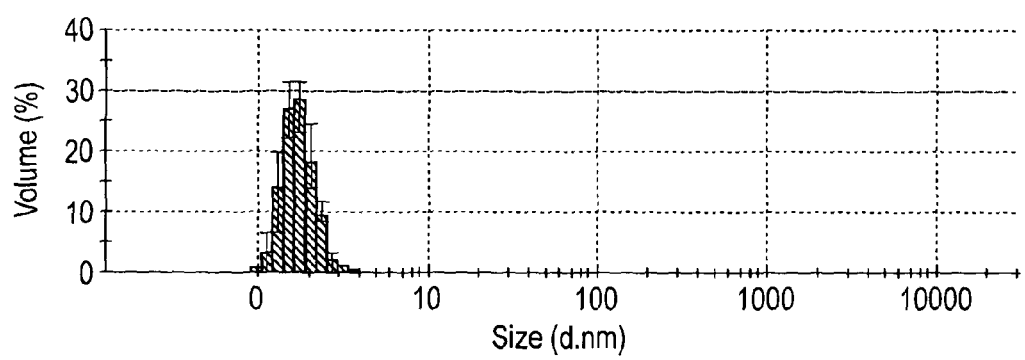
FIG. 4. Particle sizing for $Cu^{2+}_{20}$OH-Cys$_{20}$ nanoparticles after synthesis (N=3).

It should be noted that different sizes and shapes of sensors could be achieved by transferring aliquots of the final suspension to suitably shaped and sized moulds prior to cooling. As shown in FIGS. 1 to 1b, $Fe_{40}OH$ tends to form agglomerates in the absence of a matrix such as gelatin, but when incorporated in a matrix material, the physicochemical effect of matrix results in physically disperse particles at sizes below 100 nm.

Example 10

Nanoparticulate Tartrate Modified Ferrous Oxo-Hydroxide Dispersed in a Hydroxyethyl Cellulose Semi-Solid Matrix The following process was carried out under a nitrogen atmosphere. A nanoparticulate ferrous oxo-hydroxide material was prepared as described in Example 2. Next, the suspension was heated to 40° C. and then hydroxyethyl cellulose (10% w/w) was added to this suspension while stirring. A semi-solid matrix, that immobilised the ferrous oxo-hydroxide particles, formed quite rapidly after the addition of hydroxyethyl cellulose.

Example 11

Cuprous Oxo-Hydroxide, $Cu^+_{10}OH$

All solutions/suspensions were bubbled with nitrogen before and throughout the synthesis to achieve low oxygen conditions. A cuprous solution was prepared by adding cuprous chloride to water that had been previously acidified with hydrochloric acid. The final copper concentration was 10 mM and the pH was generally below 2.0 and usually about 1.0. Once all of the cuprous salt dissolved, the pH was raised with a NaOH solution to pH 7.0-9.0, usually 8.0, during which a precipitate, i.e. cuprous oxo-hydroxide, was formed. The material was initially a faint yellow colour and turned blue/green when tested in an atmosphere having 21% oxygen. Finally, this material was incorporated as a nanoparticulate dispersion in a semi-solid matrix.

Example 12

Cuprous Oxo-Hydroxide, $Cu^+_{20}OH$

Example 11 was repeated using 20 mM copper instead. An initial pH of about 1.0 was required, to ensure full dissolution of the cuprous salt, prior to commencement of the synthesis.

Example 13

Gluconate-Modified Cuprous Oxo-Hydroxide, $Cu^+_{20}OH\text{-}Gluc_{100}$

All solutions/suspensions were bubbled with nitrogen before and throughout the synthesis to achieve low oxygen conditions. A cuprous solution was prepared by adding cuprous chloride to water that had been previously acidified with hydrochloric acid and agitated until all of the cuprous salt dissolved. This solution was then added to another solution containing sodium gluconate. The solution obtained from mixing the two solutions contained 20 mM copper and 100 mM gluconate, and its pH was about 1.0-2.0. The pH was then raised with a NaOH solution to pH 7.0-9.0, usually 8.0, during which a blue/green precipitate, i.e. gluconate modified cuprous oxo-hydroxide, was formed. Finally, this suspension was used directly as a sensor, recovered through filtration for other oxygen sensing methods, or, in some preferred embodiments, dispersed in a semi-solid matrix.

Example 14

Nanoparticulate Cysteine-Modified Cuprous Oxo-Hydroxide, $Cu^+{}_{20}OH\text{-}Cys_{20}$ All solutions/suspensions were bubbled with nitrogen before and throughout the synthesis to achieve low oxygen conditions. A cuprous solution was prepared by adding cuprous chloride to water that had been previously acidified with hydrochloric acid and agitated until all of the cuprous salt dissolved. This solution was then added to another solution containing cysteine. The solution obtained from mixing the two solutions contained 20 mM copper and 20 mM cysteine, and its pH was about 1.0. The pH was then raised with a 5 M NaOH solution to pH 7.0-9.0, usually 8.0, during which a brown nanoparticulate suspension, i.e. cuprous oxo-hydroxide nanoparticles, was formed that turned black upon oxidation/sensing. Finally, this suspension was used directly as a sensor, recovered through filtration for other oxygen sensing methods, or, preferably, incorporated as a nanoparticulate dispersion in a semi-solid matrix.

Example 15

Cuprous Oxo-Hydroxide Dispersed in a Gelatin Semi-Solid Matrix

The following process was carried out under a nitrogen atmosphere. First, cuprous oxo-hydroxide was prepared as described in Example 11, 12 or 13. Next, beef gelatine (15% w/w) was added to this suspension while stirring. Then, the mixture was heated to 40° C. to dissolve the gelatine. Once the gelatine was fully dissolved, the pH was re-adjusted back to its original level with a NaOH solution. Finally, a semi-solid matrix that immobilised and dispersed the cuprous oxo-hydroxide into nanoparticles, was formed by cooling this suspension to room temperature.

Example 16

Nanoparticulate Cuprous Oxo-Hydroxide Immobilised in a Gelatin Semi-Solid Matrix The following process was carried out under a nitrogen atmosphere. A nanoparticulate cuprous oxo-hydroxide was prepared as described in Example 14. Next, this suspension was heated to 40° C. Then, beef gelatine (15% w/w) was added to this suspension while stirring. Once the gelatine was fully dissolved, the pH was re-adjusted back to its original level with a NaOH solution. Finally, a semi-solid matrix that immobilised the cuprous oxo-hydroxide nanoparticles was formed by cooling this suspension to room temperature.

Example 17

Comparison of the Sensitivity Ferrous Oxo-Hydroxide Materials Immobilised in a Gelatin Semi-Solid Matrix: $Fe^{2+}{}_{40}OH$ and $Fe^{2+}{}_{40}OH\text{-}Succ_{200}$ $Fe^{2+}{}_{40}OH$ and $Fe^{2+}{}_{40}OH\text{-}Succ_{200}$ where produced at pH 8.0 and immobilised in gelatin as described in Example 8. Prior to cooling down, 500 microliters of each suspension was dispensed under a flow of nitrogen into top-opened cylindrical moulds (1.35 cm inner radius). The sensing materials remained in the top-opened moulds for the duration of the sensing experiment and initially where kept in an oxygen free chamber (<100 ppm $O_2$). Next concentration of oxygen was raised to 0.5% to allow oxidation. After 2 h 30 min under 0.5% $O_2$, the $Fe^{2+}{}_{40}OH\text{-}Succ_{200}$ material changed from green to orange ($Fe^{2+}$ to $Fe^{3+}$ oxidation) while $Fe^{2+}{}_{40}OH$ remained green, showing that the incorporation of succinate increased sensitivity in relation to $Fe^{2+}{}_{40}OH$.

In general, it should be noted that different sizes and shapes of sensors impact on sensing time. For example, sensing materials produced in shallower moulds, than those described herein, will change colour faster, since oxygen will permeate shorter distances through the semi-solid matrix before reaching the entirety of the sensing material.

Example 18

Comparison of the Sensitivity Ferrous Oxo-Hydroxide Materials Immobilised in a Gelatin Semi-Solid Matrix: $Fe^{2+}{}_{40}OH$ and $Fe^{2+}{}_{40}OH\text{-}T_{200}$ $Fe^{2+}{}_{40}OH$ and $Fe^{2+}{}_{40}OH\text{-}T_{200}$ where produced at pH 8.0 and immobilised in gelatin as described in Examples 8 and 9. Prior to cooling down, 500 microliters of each suspension was dispensed under a flow of nitrogen into top-opened cylindrical moulds (1.35 cm inner radius). The sensing materials remained in the top-opened moulds for the duration of the sensing experiment and initially where kept in an oxygen free chamber (<100 ppm $O_2$). Next concentration of oxygen was raised to atmospheric level (21%) to allow oxidation. After 40 min under 21% $O_2$, a change from green to orange ($Fe^{2+}$ to $Fe^{3+}$ oxidation) was already visible in the $Fe^{2+}{}_{40}OH$ material while $Fe^{2+}{}_{40}OH\text{-}T_{200}$ remained green.

Nanosensors: Proof-of-Concept

Testing of Oxygen Sensors

In the examples that follow, the oxygen sensors were tested directly in suspension or trapped in a gelatine matrix. The sensors were then either exposed to atmospheric oxygen or kept in an oxygen-free environment (i.e. nitrogen). A gelatine matrix was use to stabilise some of the sensors in a 'solid form' for proof-of-principle purposes but in commercial embodiments, other materials may be used instead or in addition to gelatine.

Sensors in Suspension $Fe^{2+}{}_{40}OH\text{-}T_{200}$ is a nanoparticulate ferrous oxo-hydroxide modified with tartaric acid, which is dark green, but upon exposure to oxygen, the solution changes to orange/brown. This is due to the oxidation of ferrous iron ($Fe^{2+}$) as ferrous oxo-hydroxide to ferric iron ($Fe^{3+}$). Similar results were obtained with a different ratio of iron to tartaric acid ($Fe^{2+}{}_{40}OH\text{-}T_{120}$ but the colour change was found to occur more rapidly.

Succinate and citric acid were also used as ligands and the resulting ferrous oxo-hydroxides showed similar behaviour. The colour of $Fe^{2+}{}_{40}OH\text{-}T_{200}Succ_{200}$ changed from green to orange/brown upon oxidation. The nanoparticulate suspension is lighter in colour and more precipitate is formed upon oxidation than with $Fe^{2+}_{40}OH-T_{200}$, but the colour change was still clearly seen.

Sensors in a Solid Matrix

Unmodified (i.e. with no added ligands) and tartrate-doped ferrous oxo-hydroxides were immobilised and nano-dispersed in a gelatine matrix as proof of principle. Advantageously, the change of the colour in the solid matrix was even more defined than the colour change in solution. Without wishing to be bound by any particular theory, the present inventors believe that the alteration in colour observed in these experiments using a matrix material such as gelatine may be due to the incorporation of pendant groups from the matrix into the ferrous oxo-hydroxide material, and indicates that these pendant groups present in the matrix material may, given the right synthetic conditions, alter the physicochemical properties of metal ion oxo-hydroxide materials in a similar fashion to free ligands, such as tartrate.

Overall, these results show that we can apply these oxygen sensors to packaging by incorporating them in a matrix such as gelatine and suggest that other ingredients that can form a gel or solid matrix, such as starch or cellulose, can be used. Also, this work showed that different sensitivity can be obtained by producing sensors at different pH's. The use of hydrated matrices also permits other components to be added to the sensors such as other redox sensitive materials, including M containing materials, minerals, compounds or complexes.

Oxygen Indicator in Powder Form

We have investigated the use of dry powders of unmodified and tartrate-doped ferrous oxo-hydroxides as sensors, as dry powders may be preferred for some applications, such as surface coating. The unmodified ferrous oxo-hydroxide powder was originally green, but slight oxidation during the drying process altered it to brownish green. Nevertheless, subsequent exposure to oxygen resulted in further colour change showing that the dry powder, if dried in an oxygen free environment, can be used as a sensor. The tartaric-doped ferrous oxo-hydroxide powder showed a more subtle, and slower, colour change compared to the unmodified ferrous oxo-hydroxide indicating that the sensitivity of sensors based in dry powders may be tailored by ligand modification.

Reactivation of Oxidized Indicators

The packaging process may result in a partial oxidation of the sensor due to unintended exposure to oxygen. We have found evidence that it is possible to reactivate the sensors of the present invention by exposing them to high temperatures (>80° C.) We have also found that this reactivation process is significantly more efficient if in the presence of reducing sugars, such as glucose or fructose.

Copper-Based Sensor

Copper is a transition metal which also forms oxo-hydroxides at high pH and that changes colour when oxidised (cuprous [$Cu^+$] to cupric [$Cu^{2+}$]). The colour change of unmodified cuprous oxo-hydroxide in a gelatine matrix was originally very light ($Cu^+_{10}OH$) to dark yellow ($Cu^+_{20}OH$) to blue greenish ($Cu^{2+}$) in the presence of oxygen. $Cu^+_{10}OH$ appeared transparent but in fact was a very faint yellow.

Tailoring of Sensitivity Via Incorporation of Ligands

The incorporation of ligands into the metal ion oxo-hydroxide materials can be used to either increase sensitivity (e.g. $Fe^{2+}_{40}OH-Succ_{200}>Fe^{2+}_{40}OH$ sensitivity) or to decrease it ($Fe^{2+}_{40}OH-T_{200}$ sensitivity<$Fe^{2+}_{40}OH$ sensitivity). Without wishing to be bound by a particular theory, the present inventors believe that increased sensitivity appears is achieved by incorporating ligands with low affinity for the metal ion, while the incorporation of higher affinity ligands seems to stabilise the materials at low valence states, thereby decreasing their sensitivity for oxygen.

All documents mentioned in this specification are incorporated herein by reference in their entirety.

The invention claimed is:

1. A product packaging for storing an article in a packaging envelope under modified atmosphere conditions, said product packaging comprising an oxygen sensor comprising a solid poly oxo-hydroxy metal ion material having a transition metal ion in a first oxidation state that is capable of oxidation to a second oxidation state in response to oxygen, said solid poly oxo-hydroxy metal ion material having a polymeric structure in which one or more ligands are non-stoichiometrically substituted for the oxo and/or hydroxy groups, wherein exposure of the sensor to oxygen leaking into the packaging envelope causes the oxidation of the metal ion in the solid poly-oxo-hydroxy material to the second oxidation state, producing a detectable change in the material.

2. The product packaging of claim 1, wherein the solid poly-oxo-hydroxy metal ion material is present in nanoparticulate or nanostructured form.

3. A product packaging for storing an article in a packaging envelope under modified atmosphere conditions, said product packaging comprising an oxygen sensor comprising a solid oxo-hydroxy metal ion material having a transition metal ion in a first oxidation state that is capable of oxidation to a second oxidation state in response to oxygen, said solid oxo-hydroxy metal ion material being present in nanoparticulate or nanostructured form, wherein exposure of the sensor to oxygen leaking into the packaging envelope causes the oxidation of the metal ion in the solid oxo-hydroxy material to the second oxidation state, producing a detectable change in the material.

4. The product packaging of claim 1, wherein the metal ion material is present in a hydrated, oxygen permeable matrix so that oxygen permeating the matrix causes the oxidation of the metal ion to produce a detectable change in the material.

5. The product packaging of claim 4, wherein the metal ion material does not form a soluble complex with materials forming the matrix.

6. The product packaging of claim 3, wherein the metal ion material has a polymeric structure in which one or more ligands are non-stoichiometrically substituted for the oxo and/or hydroxy groups.

7. The product packaging of claim 1, wherein the oxo and/or hydroxy groups are non-stoichiometrically substituted by one or more ligands selected from phosphate, sulphate, silicate, nitrite, nitrate, selenate and/or bicarbonate.

8. The product packaging of claim 1, wherein the oxo and/or hydroxy groups are non-stoichiometrically substituted by phosphate and where phosphate becomes the dominant mineral phase above the oxo-hydroxide mineral phase.

9. The product packaging of claim 1, wherein the oxo and/or hydroxy groups are non-stoichiometrically substituted by silicate and where silicate becomes the dominant mineral phase above the oxo-hydroxide mineral phase.

10. The product packaging of claim 1, wherein the colour change is irreversible under normal use in the modified atmosphere packaging.

11. The product packaging of claim 1, wherein the detectable change is a visible colour change.

12. The product packaging of claim 1, wherein the detectable change is detectable under UV light.

13. The product packaging of claim 1, wherein the metal ion is copper, iron, chromium, vanadium, manganese, titanium, cobalt, molybdenum and/or tungsten.

14. The product packaging of claim 1, wherein the metal ion is copper and/or iron.

15. The product packaging of claim 1 wherein the transition metal ion is (a) iron and the first oxidation state is Fe(II) and the second oxidation state is Fe(III); or (b) copper and the first oxidation state is Cu(I) and the second oxidation state is Cu(II); or (c) cobalt and the first oxidation state is Co(II) and the second oxidation state is Co(III).

16. The product packaging of claim 1, wherein the matrix is formed from gelatine, agar, agarose, a cellulosic material, or a combination thereof.

17. The product packaging of claim 1, wherein the matrix comprises between 0.01% and 25% w/w of the solid metal ion material.

18. The product packaging of claim 1, wherein the matrix is a semi-solid matrix, a solid format, or an aqueous suspension.

19. The product packaging of claim 1, wherein the oxygen sensor is a powder or is surface coated.

20. A method of detecting oxygen leaking into product packaging for storing an article in a packaging envelope under modified atmosphere conditions, the method comprising:
  (a) providing an oxygen sensor according to claim 1 within the packaging envelope under modified atmosphere conditions, so that oxygen leaking into the packaging envelope causes oxidation of the metal ion to produce a detectable change in the material; and
  (b) optionally detecting the change in the material to indicate the leakage of oxygen into the packaging envelope.

21. The method of claim 20, wherein the packaging is for a product selected from a food product, a pharmaceutical product, a nutraceutical product, a document, book or manuscript, or an electronic device or component.

* * * * *